US00PP18892P3

(12) United States Plant Patent
Way et al.

(10) Patent No.: US PP18,892 P3
(45) Date of Patent: Jun. 10, 2008

(54) 'NEWFANE' SWEET CHERRY TREE
*PRUNUS AVIUM*

(50) Latin Name: *Prunus avium*
Varietal Denomination: Newfane

(75) Inventors: Roger D. Way, Stanley, NY (US); Susan K. Brown, Geneva, NY (US); Robert Anderson, Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 267 days.

(21) Appl. No.: 09/894,352

(22) Filed: Jun. 27, 2001

(65) Prior Publication Data

US 2003/0005496 P1 Jan. 2, 2003

(51) Int. Cl.
*A01H 5/00* (2006.01)

(52) U.S. Cl. ..... Plt./181

(58) Field of Classification Search ..... Plt./181
See application file for complete search history.

*Primary Examiner*—Kent Bell
(74) *Attorney, Agent, or Firm*—Flynn, Thiel, Boutell & Tanis, P.C.

(57) ABSTRACT

A new and distinct variety of sweet cherry tree, *Prunus avium,* originating as a hybrid seedling of the cross: 'Emperor Francis' (non-patented)×'Stella' (non-patented). This new variety is unique from its parents and other sweet cherries varieties because it is a light fleshed, light skinned variety that is suitable for brining users and is self-fertile.

2 Drawing Sheets

FIELD OF THE INVENTION

A new and distinct variety of sweet cherry tree that originated as a seedling of *Prunus avium* in the breeding program of Cornell University and is hereinafter referred to as 'Newfane' sweet cherry. This new variety is unique because this is the first self-fertile, yellow flesh-type, sweet cherry that has been made available to the commercial nursery industry of the United States of America; and the fruit has several traits that make if favorable for dual-purpose fresh market and processed uses.

SUMMARY OF THE INVENTION

This new and distinct variety of sweet cherry was discovered in 1984 by Roger D. Way (retired), a plant breeder at the New York State Agricultural Experiment Station, Geneva, N.Y., a research unit of Cornell University, hereinafter referred to as Geneva Experiment Station. By breeding methodology convention at the Geneva Experiment Station it was designated as NY 13688. This selection was initially assigned Experiment Station Breeding Record Number 75.304, a hybrid population of trees that resulted from hybridizing the varieties 'Emperor Francis' (non-patented)×'Stella' (non-patented) in 1975, and this seedling was designated as NY 13688 when it was planted in 1976 as part of a population of 433 siblings possessing the same parentage. The orchard location where the seedling was grown and first noticed was designated as Crittenden Farm, Field Number 30, Row 5, Tree 010. This seedling was first noticed because in 1984 Cornell scientists purposely bagged branches to isolate the flowers from pollinating insect visits and it cropped heavily inside the bag, proving that it was self-fertile; and the fruit were light in flesh color and possessed a ninety percent red blush. This skin coloration was considered as uncommon and potentially valuable for fresh market appeal of the fruit. The new variety has been propagated on Mazzard seedling (non-patented), Mahaleb seedling (non-patented), 'Gisela 6' (U.S. Plant Pat. No. 8,954), 'MxM 2' (U.S. Plant Pat. No. 8,194) and 'MxM 60' (U.S. Plant Pat. No. 8,132) rootstocks and remains true to the description herein.

The new variety differs from its parents in the following. Unlike 'Emperor Francis' (not patented) the new variety is self fertile whereas 'Emperor Francis' (non patented) requires another variety as a pollen source. Unlike 'Stella' (non patented) the new variety is yellow fleshed with skin coloration of a red blush over yellow where "Stella" (non patented) has dark burgundy-black skin and flesh.

A BRIEF DESCRIPTION OF THE DRAWINGS

The accompanying photographs show typical specimens of the new variety as depicted in color as nearly true as is reasonably possible in color illustrations of this character. These specimens were obtained at the Geneva Experiment Station, Geneva, N.Y.

Figure 1:
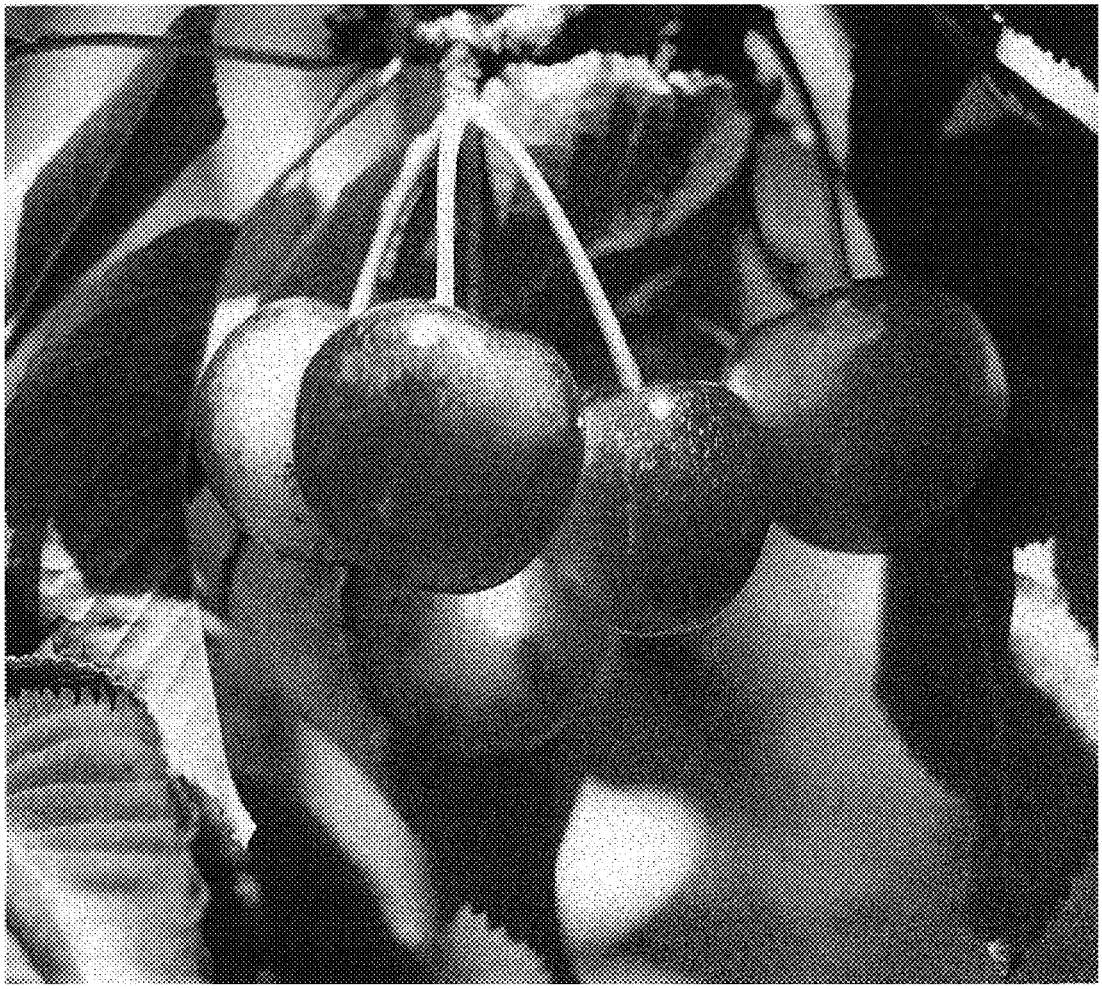

FIG. 1. Illustrates the intact fruit and foliage of the new variety at maturity.

Figure 2:
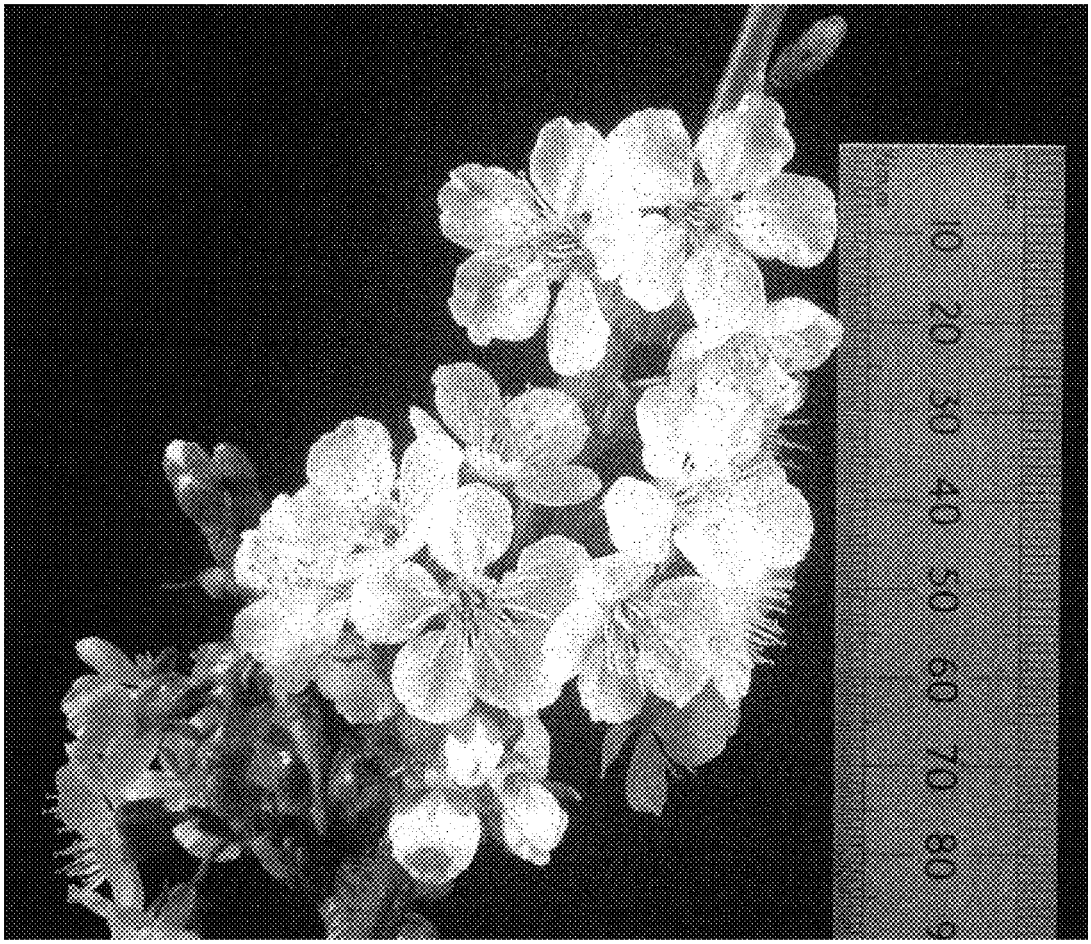

FIG. 2. Illustrates the blossoms of the new variety.

A BOTANICAL DESCRIPTION OF THE PLANT

A detailed description of the 'Newfane' sweet cherry cultivar follows using The Royal Horticultural Society of London Colour Chart for color identification except where general color terms are sufficient.

Locality of the original discovery and observations is the Crittenden Farm Research Orchard Number 30, Row 5, tree 010 (assigned the designation NY 13688), Geneva Experiment Station, Geneva, N.Y., U.S.A.

Parentage: A hybrid seedling of the cross: 'Emperor Francis' (non-patented)×'Stella' (non-patented).

Tree:

*Age of specimen.*—25 years old.

*Height.*—5 M.

*Width.*—4.5 M.

*Size.*—68 cm in diameter at 100 cm above ground level.

*Vigor.*—Medium.

*Density.*—Medium.

*Form.*—Upright spreading, with medium level of lateral branching.

*Production.*—Heavy, 200 to 250 pounds per tree per season.

*Bearing.*—Annual on spurs and on 3 to 4 bud positions located at the base of one year old shoots.

*Disease resistance.*—Similar to 'Emperor Francis' (non-patented) in tolerance to brown rot fungus of the blossoms and fruit (rated 7 at Geneva on scale of 1, as worst, to 9, as best); also similar to 'Emperor Francis' (non-patented) in tolerance to bacterial canker of the tree and fruit (rated 8 at Geneva on scale of 1, as worst, to 9 as best); highly tolerant of black knot fungus of the wood.

*Cold hardiness.*—Good, crops regularly in test orchards in commercial fruit districts of New York and Michigan.

*Graft compatibility.*—Good, produces compatible graft unions with Mazzard seedling (non-patented), Mahaleb seedling (non-patented), 'Gisela 6' (U.S. Plant Pat. No. 8,954), 'MxM 2' (U.S. Plant Pat. No. 8,194) and 'MxM 60' (U.S. Plant Pat. No. 8,132) cherry rootstocks.

Trunk:

*Size.*—68 cm in diameter at 100 cm above ground.

*Surface.*—Bark is smooth with prominent lenticels.

*Bark color.*—Grayed Orange Group 166A where directly exposed to the sun.

*Lenticels.*—Varying in length from 1.5 to 3.0 cm and width from 0.25 to 0.5 cm, prominent, horizontal, elliptical.

*Lenticel color.*—Grayed Orange 167A.

Branches:

*1 year old branches.*—Average length 33 cm, width 4 cm, internode distance 33 cm, color Grayed Orange 166B.

*2 year old branches.*—Average length 42 cm, width 6 cm, internode distance 30 cm, color Grayed Orange 166A.

*Lenticils.*—Few, scattered, color Grayed Yellow 161B.

Vegetative buds:

*Placement.*—At bud positions 4 and higher numbered from the base of new growth, and at tip of each fruit spur.

*Appearance.*—Pointed and flatter than flower buds on previous season's annual growth of shoots.

*Color.*—Yellow Green 144 B.

Leaves:

*Size.*—9.0 to 10.5 cm in length, 5.5 to 6.25 cm in width with petiole 6.0 to 6.5 cm in length.

*Form.*—Symmetrical halves on both sides of central axis, asymmetrical tapering with taper from petiole to about three fourths of the length gradual to this its widest point and sharply tapered back to the apex.

*Thickness.*—Medium.

*Margin.*—Serrations regular and bluntly pointed.

*Adaxile surface.*—Green Group 137B.

*Abaxile surface.*—Yellow Green Group 148B.

*Texture.*—Leathery with a crisp feeling.

*Pubescence.*—None on either surface.

*Petiole length.*—6.5 to 7 cm.

*Petiole color.*—Adaxial Red Purple 59 A, abaxial Yellow Green 146 C.

*Petiole groove.*—Narrow.

*Veination.*—Pinnate.

*Vein color.*—Green 137 C on adaxial surface, Yellow Green 144 B on abaxial surface.

*Glands.*—2 to 3 on petiole, globose tending to oblong, length 2.5 to 3 mm, width 1 mm.

*Gland color.*—Yellow Green 144 B with a blush of Green Orange 172 A.

Flower buds:

*Size.*—Length 11 cm, width 4 cm.

*Form.*—Elongated oval.

*Color.*—Green 143B.

*Peduncle.*—Length 6 cm, width 0.8 cm, color Green 143B.

*Number of buds per spur.*—3 to 7, average of 5.

Flowers:

*Blooming period.*—Mid season, April 25 to April 28 in Geneva, N.Y.

*Presentation.*—Showy white.

*Fertility.*—Self-fertile.

*Pollen.*—Present, plentiful, good pollen source for pollenizing all other sweet cherries that bloom at the mid-season sequence, color Yellow 13B.

*Corolla diameter.*—33 mm.

*Number of flowers per cluster.*—3 to 7.

*Petals.*—Single, round, length 12 mm, width 12 mm, 5 in number, separate, margin wavy at apex, soft texture, White 155 D.

*Peduncle.*—4.2 mm. in length and 0.35 mm in width.

*Filament.*—Length 8 mm, width 0.1 mm, white 155 D.

*Anther.*—Profuse pollen, Yellow 13 B.

*Sepals.*—5 in number, Green 143 C, bluntly pointed at apex.

Fruit:

*Maturity when described.*—Commercial ripeness, 17 degrees brix.

*Date of first picking.*—Mid-season ripening, July 7 to 10th of Geneva, N.Y.

*Size.*—Weight: 9 g, length: 3.1 cm, width: 2.8 cm.

*Form.*—Round-oblong appearance; fruit tapers from widest dimension on cheeks toward stigmatic scar and gives the appearance of slightly heart shape.

*Stem.*—Length 37 mm, width 1.5 mm, color Green 143 B.

*Stem scar.*—Dry when machine harvested without stems.

*Stem cavity.*—Wide, not prone to concentric cracks from rain settling in the cavity.

Skin:

*Thickness.*—Medium.

*Tendency to crack.*—Similar to 'Emperor Francis' (non patented), rated as 6 at Geneva (1, worst to 9 best), may split on shoulders in high rainfall seasons.

*Color.*—Blush of skin is Red Group 42A, ground coloration of skin is Yellow Group 11B.

*Flavor.*—Good.

Flesh:

*Texture.*—Medium firm, rated as 6 at Geneva (1, worst to 9 best).

*Acidity.*—Medium high until sugar level gets to above 15 degrees brix.

*Flavor.*—Good.

*Aroma.*—Pleasant, pleasing.

*Color.*—Yellow Group 3 A.

*Coloration in the pit cavity.*—Same as flesh.

*Juice.*—Plentiful, very sweet.

*Eating quality.*—Good when mature to above 16 degrees brix, slightly acid if eaten when immature.

Stone:

*Size.*—1.6 cm in length, 1.3 cm in width at widest point near the center, 0.8 cm in width at widest point of the flatter direction.

*Form.*—Slightly oblong.

*Sides.*—Ridges, 4 to 5 in number, with varying amounts of encircling the suture side of the pit.

*Tendency to crack.*—None observed.

*Type.*—Freestone at commercial maturity.

Use: Dual purpose for either fresh market or processed as brined; may become popular for commercial orchardists to use as pollenizer because universally compatible with all other sweet cherry varieties and has unique fruit coloration which will allow it to be easily identified by harvest laborers as they differentiate between dark-type fruit and this variety; may become popular for home orchards where light flesh-type is desired if lawn/garden space is limited because self-fertile trait allows successful cultivation of just one sweet cherry tree.

What is claimed:

1. A new and distinct variety of sweet cherry tree, *Prunus avium,* substantially as herein shown and described, characterized as to novelty by the unique combination of self-fertile flowers, light flesh-type, with good disease tolerance and good hardiness of the tree; and possessing fresh market eating quality and shipping/handling attributes that meet grade standards for this fruit and possessing processing attributes as required for brining uses.

* * * * *